(12) United States Patent
Menta et al.

(10) Patent No.: US 6,333,346 B1
(45) Date of Patent: Dec. 25, 2001

(54) UREIDO AND THIOUREIDO DERIVATIVES OF 4-AMINO-2(5H)-FURANONES AND 4-AMINO-2(5H)-THIOPHENONES AS ANTITUMOR AGENTS

(75) Inventors: Ernesto Menta, Cernusco sul Naviglio; Nicoletta Pescalli, Adda; Marco Conti, Milan, all of (IT); Gerd Zimmerman, Mannheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/485,709

(22) PCT Filed: Sep. 1, 1998

(86) PCT No.: PCT/EP98/05524

§ 371 Date: Jun. 2, 2000

§ 102(e) Date: Jun. 2, 2000

(87) PCT Pub. No.: WO99/12917

PCT Pub. Date: Mar. 18, 1999

(30) Foreign Application Priority Data

Sep. 5, 1997 (EP) .................................................. 97115391

(51) Int. Cl.$^7$ ..................... A61K 31/341; A61K 31/381; C07D 307/30; C07D 333/32
(52) U.S. Cl. ..................... 514/445; 514/447; 514/472; 514/473; 549/63; 549/66; 549/321; 549/323
(58) Field of Search ..................... 549/321, 323, 549/63, 66; 514/445, 447, 472, 473

(56) References Cited

U.S. PATENT DOCUMENTS

Re. 27,894   1/1974   Gerike et al. ..................... 260/343.6

OTHER PUBLICATIONS

Hiyama et al., "Synthesis of 4–amino–2(5H)–furanones through intra–and intermolecular nitrile addition of ester enolates . . . ", Bull. Chem. Soc. JPN., 87, vol. 60 (6) pp 2139–2150.
Patent Abstracts of Japan, vol. 012, No. 450, Nov. 25, 1998, JP 63 174983, Jul. 19, 1988.

*Primary Examiner*—Ba K. Trinh
(74) *Attorney, Agent, or Firm*—Arent Fox Kintner Plotkin & Kahn PLLC

(57) ABSTRACT

The present invention relates to ureido and thioureido derivatives of 4-amino-2(5H)-furanones and 4-amino-2 (5H0-thiophenones for the treatment of tumors.

5 Claims, No Drawings

UREIDO AND THIOUREIDO DERIVATIVES OF 4-AMINO-2(5H)-FURANONES AND 4-AMINO-2(5H)-THIOPHENONES AS ANTITUMOR AGENTS

This application is a 371 of PCT/EP98/05524 dated Sep. 1, 1998.

The present invention relates to ureido and thioureido derivatives of 4-amino-2(5H)-furanones and 4-amino-2 (5H)-thiophenones which were found to possess a marked antitumor activity, especially against colon cancers.

BACKGROUND OF THE INVENTION

Colo-rectal carcinoma is one of the most common tumors in industrialized world; with an incidence of approximately 421,000 new cases/year world-wide, it is second only to lung and mammary tumors in causing death. The rate of patients curable with surgery only is approximately 45–50%. The others may be treated with combination chemotherapy which allows to a complete remission rate of no more than 5%.

Colo-rectal tumors are usually refractory or poorly sensitive to available chemotherapy and the only agent which provides some responses against this cancer is 5-Fluorouracil.

So far no therapeutic alternatives exist after the failure of the first-line combination chemotherapy essentially based on 5-FU.

Despite many new investigational agents are undergoing preclinical and clinical studies against colorectal cancer, it is generally believed that only compounds with innovative structures and possible new mechanisms of action may be successful against this highly refractory tumor hystotype.

Therefore the search for new active drugs in this indication still represents one of the most interesting and attractive field in oncology.

We have now discovered a new class of compounds, namely 4-ureido and thioureido 2(5H)-furanones, respectively 2(5H)-thiophenones, which possesses a marked antitumor activity, especially against colon cancers.

Phenylureido furanones have been already described having activity as defoliants (Reissue U.S. Patent 27,894), as herbicides (JP 63-174983) or in Bull.Chem.Soc.Jpn. Vol. 60, 2139ff as intermediates. However, no pharmaceutical activity, especially antitumour activity, has been reported in these documents. Only DE-A-25 16 555 describes 1-tert.alkyl-3-(substituted furyl)-urea-derivatives with an antihypertensive activity.

DESCRIPTION OF THE INVENTION

Object of the present invention are compounds of the general formula (I):

(I)

wherein:
A is oxygen or sulfur;
X is oxygen or sulfur;
R1 and R2 are independently hydrogen or an alkyl group woth from 1 to 6 carbon atoms;

R is selected from: $(C_1-C_{10})$alkyl, $(C_3-C_7)$cycloalkyl, naphthyl, phenyl, phenyl substituted by from 1 to 3 groups selected from: $(C_1-C_4)$alkylthio, $(C_1-C_4)$alkylsulphinyl, $(C_1-C_4)$alkylsulphonyl, $(C_1-C_4)$hydroxyalkyl, $(C_1-C_4)$; chlorine, bromine, iodine or fluorine; $(C_1-C_4)$perfluoroalkyl; hydroxy; $(C_1-C_4)$alkoxy; amino; mono- or di-$(C_1-C_4)$alkylamino; aminosulphonyl; $(C_1-C_4)$alkylsulphonamido; phenyl- or tolyl-sulphonoamido; carboxy; $(C_1-C_4)$alkoxycarbonyl; amidocarbonyl or $(C_1-C_4)$alkylamidocarbonyl; carboxaldehyde; $(C_1-C_4)$alkylcarbonyl; nitro; phenylthio; cyanomethyl, and optionally substituted phenyloxy or optionally substituted phenyl-$(C_1-C_4)$-alkyl or R is a 5- or 6-membered aromatic or non-aromatic heterocycle containing from 1 to 3 heteroatoms selected from oxygen, sulfur and nitrogen, which can be optionally benzocondensed, with the proviso, that when A is oxygen and X is oxygen, R is not $(C_1-C_{10})$ alkyl.

the pure stereoisomers or mixtures thereof as well as salts thereof with pharmaceutically acceptable acids or bases, for the use as medicaments, in particular as antitumor agents. When R is a heterocycle, it is preferably selected from pyridine, pyrrole, thiazole, thiophene, furane, imidazole, pyrazine, pyrimidine, quinoline, isoquinoline, indole, 3,4-methylenedioxyphenyl, piperazine, piperidine, morpholine and pyrrolidine.

The compounds in which R is an unsubstituted phenyl group or $(C_1-C_{10})$ alkyl and X is oxygen are known (US-Re 27,894; JP 63-174983; DE-A-2 516 555 and Bull.Chem-.Soc.Jpn. Vol. 60, 2139ff). Therefore, another object of the present invention are new compounds of formula (I), with the proviso that, when X is oxygen, R is not an unsubstituted phenyl group or $C_1-C_{10}$ (alkyl).

Preferred compounds of formula (I) are those in which X is oxygen, R1 and R2 are hydrogen and R is a substituted phenyl group.

Particularly preferred compounds of formula (I) are:
4-[N-(4-chlorophenyl)aminocarbonylamino]-2(5H)-furanone;
4-[N-(4-ethyl-3-chlorophenyl)aminocarbonylamino]-2(5H)-furanone.

A further object of the present invention is to provide processes for the preparation of the compounds of formula (I).

A still another object of the present invention are pharmaceutical formulations containing a pharmaceutically effective dosage of one or more compounds of formula (I) in admixture with pharmaceutically acceptable excipients.

PREPARATION OF THE COMPOUNDS OF THE INVENTION

The compounds of formula (I) wherein A is oxygen, can be prepared by reacting bromo- or chloro-acetoacetate of formula (II):

(II)

wherein R1 and R2 have the above meanings, H₂l is bromine or chlorine and Y is a lower alkyl group, with an urea or thiourea of formula (III)

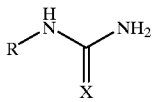
(III)

wherein R and X have the above meanings, preferably in a solvent and at temperatures ranging from room temperature to the boiling temperature of the solvent, as described in US-Re 27,894, which is herein incorporated by reference.

The preparation of intermediates of formula (II) and (III), which are mainly commercial and widely known products, is also described in US-Re 27,894.

An alternative process comprises the reaction of a 4-amino-2(5H)furanone of formula (IV):

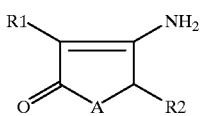
(IV)

wherein A is oxygen or sulfur and $R_1$ and $R_2$ have the above-mentioned meanings, with an isocyanate or an isothiocyanate of formula (V):

 (V)

as described in JP 63-174983, which is herein incorporated by reference. The reaction comprises the formation of a sodium salt of intermediate of formula (IV) (by reaction with sodium hydride at 40–50° C.), followed by the condensation reaction with the compound of formula (V) at about 50° C. The use, in the first step, of a different strong base at temperatures ranging from 0° C. to 100° C. can be also advantageously provided.

A still alternative process is to react intermediates of formula (IV) with 1,1'-carbonyl diimidazole or 1,1'-thiocarbonyl diimidazole, respectively, followed by reaction with an amine of formula (VI) R—NH₂.

Another alternative process is to react a compound of formula (VII):

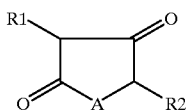
(VII)

wherein A is oxygen or sulfur and $R_1$ and $R_2$ have the above-mentioned meanings, with an urea or thiourea of formula (III), in solution at reflux or at 50 to 150° C., preferably at 80 to 120° C., without solvent and, if necessary to achieve a clear melt, a small amount of a high boiling solvent e.g. toluene, xylene, dioxane, dimethylformamide, nitromethane or n-butanol.

The synthesis of the 4-aminofuranones of formula (IV) is described in Bull. Chem. Soc. Jpn., 60, 2139-50 (1987), which is herein incorporated by reference. When R1 and R2 are both hydrogen, the compound of formula (IV) can be obtained by fusion of the corresponding compound of formula (VII) with ammonium acetate.

The compounds of formula (V) and (VI) are commercial and known compounds, which can be prepared according to methods which are part of the general knowledge of the chemist.

The compounds of formula (VII) can be prepared by heating the halogen-acetoacetates of formula (II) in a solvent.

BIOLOGICAL ACTIVITY OF THE COMPOUNDS OF THE INVENTION

The compounds of the invention were tested against three human colon tumor cell lines (HT 29, HCT 116 and LoVo). After 144 hours of incubation of the cells with the compound to be tested, the cytotoxicity is evaluated using the MTT assay (Mosman, T. "Rapid Colorimetric Assay for Cellular Growth and Survival: Application to Proliferation and Cytotoxicity Assay"; J. Immunol. Methods, (1983), 65, 66; Green, L. M., "Rapid Colorimetric Assay for Cell Viability; Application to the Quantitation of Cytotoxic and Growth Inhibitory Lymphokines", J. Immunol. Methods, (1984), 70, 257–268). The results are expressed as $IC_{50}$ (Tg/ml), that it the concentration of the tested compound which causes the death of 50% of cell population.

The data for two representative compounds of the invention are shown in table I.

TABLE I

Cytotoxic activity of the compounds of the invention against human colon cancer cell lines HT 29, HCT 116 and LoVo.

| structure | example | HT 29 $IC_{50}$ (Tg/ml) | HCT 116 $IC_{50}$ (Tg/ml) | LoVo $IC_{50}$ (Tg/ml) |
|---|---|---|---|---|
| 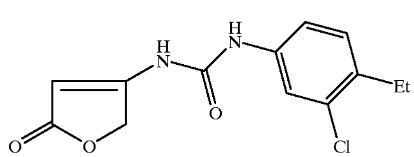 | 3 | 0.003 | <0.01 | 0.034 |

TABLE I-continued

Cytotoxic activity of the compounds of the invention against human colon cancer cell lines HT 29, HCT 116 and LoVo.

| structure | example | HT 29 IC$_{50}$ (Tg/ml) | HCT 116 IC$_{50}$ (Tg/ml) | LoVo IC$_{50}$ (Tg/ml) |
|---|---|---|---|---|
| (structure shown) | 2 | 0.032 | 0.034 | 0.01 |

From the above data it appears that the compounds of the invention are endowed with a marked activity against the colon cancers.

The compounds of the present invention can be administered in doses ranging from 0.01 mg to 0.4 g per kilogram of body weight daily. A preferred dosage regimen to obtain best results is that which provides for the use from about 1 mg to about 50 mg per kilogram of body weight daily, employing unitary doses so that to administer in 24 hours from about 70 mg to about 3.5 g of the active compound to a patient having approximately 70 kg of body weight. Such a dosage regimen may be adjusted to achieve the best therapeutical effect. For example, doses may be administered taking into account the therapeutical situation of the patient. The active compound may be administered by oral, intravenous, intramuscular or subcutaneous route.

The pharmaceutical compositions of the present invention contain therapeutical effective amounts of at least one compound of the invention in admixture with pharmaceutically compatible excipients.

Oral compositions will generally include an inert diluent or an edible carrier. They can be included in gelatin capsules or compressed into tablets. Other oral administration forms are capsules, pills, elixirs, suspensions or syrups.

The tablets, pills, capsules and similar compositions can contain the following ingredients (in addition to the active compound): a binder such as microcrystalline cellulose, tragacanth or gelatin; an excipient such as starch or lactose; a disintegrating agent such as alginic acid, primogel, maize starch and the like; a lubricant such as magnesium stearate; a fluidifier such as colloidal silicon dioxide; a sweetening agent such as sucrose or saccharine or a flavoring agent such as mint flavor, methyl salicylate or orange flavor. When the composition selected is in form of capsules, it can contain in addition a liquid carrier such as a fat oil. Other compositions can contain various material which change the physical form thereof, for example coating agents (for tablets and pills) such as sugar or shellac. The material used in the preparation of the compositions should be pharmaceutically pure and non toxic at the used dosages.

For the preparation of pharmaceutical compositions for the parenteral administration, the active ingredient can be included in solutions or suspensions, which can comprise in addition the following components: a sterile diluent such as water for injections, saline solution, oils, polyethylene glycols, glycerin, propylene glycol or other synthetic solvents; antibacterial agents such as benzyl alcohol; antioxidants such as ascorbic acid or sodium bisulfite; chelating agents such as ethylenediaminotetracetic acid; buffers such as acetates, citrates or phosphates and agents for adjusting the tonicity of the solution, such as sodium chloride or dextrose. The parenteral preparation can be included in ampoules, mono-dose syringes, glass or plastic vials.

The Following examples further illustrate the invention.

EXAMPLE 1

4-[N-(phenyl)aminocarbonylamino]-2(5H)-furanone

A mixture of N-phenylurea (1.36 g) and 2,4(3H,5H)-furandione (0.5 g) in 1 ml of ethanol is refluxed for 8 hours and the product which separates is recovered by filtration, to give, after recrystallization from dioxane, 0.38 g of the product, m.p. 238–239° C.

TLC (silica gel, eluant methylene chloride/methanol 9:1; UV detection at 254 nm): single spot at $R_f$=0.44.

Elem. Anal. (% calcd/found): C 60.55/59.46; H 4.62/4.67; N 12.84/12.96.

EXAMPLE 2

4-[N-(4-chlorophenyl)aminocarbonylamino]-2(5H)-furanone

To a magnetically stirred suspension of 4-chlorophenylurea (2 g) in dioxane (4 ml), ethyl 4-chloroacetoacetate (1.63 ml) are added and the suspension is heated to reflux for two hours, then kept at toom temperature overnight. The yellowish gray precipitate is recovered by filtration and washed with the mother liquor, with methanol (2×1 ml) and finally with diethyl ether (2 ml). After drying under vacuum at 40° C. overnight, 1.34 g of crude product were obtained. The crude product is then suspended under reflux in 20 ml of dioxane for 45 minutes, then the suspension is allowed to return to room temperature and the solid is recovered by filtration and washed with dioxane (1 ml) and then with diethyl ether (2 ml). After drying overnight under vacuum at 40° C., 1.1 g of the product are obtained, which still contains some impurities.

It is therefore dissolved in hot dimethylformamide (2.2 ml) and when a complete solution is obtained the heating bath is removed and the product reprecipitate in a short time. When the suspension reaches room temperature 11.2 ml of acetone are added and after stirring for 2 hours the solid is recovered by filtration and washed first with the mother liquor and then with acetone (2×3 ml). After drying under vacuum at 40° C. overnight, 0.73 g of off-white product are obtained, m.p.>254–256° C.

TLC (silica gel, eluant methylene chloride/methanol 9:1; UV detection at 254 nm): single spot at $R_f$=0.39.

Elem. Anal. (% calcd/found): C 52.29/52.05; H 3.59/3.60; N 11.09/10.99; Cl 14.03/14.05.

EXAMPLE 3

4-[N-(4-ethyl-3-chlorophenyl)aminocarbonylamino)-2(5H)-furanone

To a magnetically stirred suspension of 3-chloro-4-ethylphenylurea (3.43 g) in 17 ml of dioxane, ethyl 4-chloroacetoacetate (2.4 ml) are added and the resulting dark solution is refluxed for 2 hours. The reaction mixture is then kept overnight at roome temperature to give a precipitate which is recovered by filtration and washed with the mother liquor, with dioxane (2×2 ml) and with diethyl ether (2×2 ml). After drying under vacuum at 40° C. overnight 0.88 g of the crude product are obtained.

This material is suspended in 10 ml of 1 N potassium hydrogencarbonate for 30 minutes, then it is recovered by filtration and dried under vacuum at 40° C. to give 0.7 g of a residue which is dissolved in dimethylformamide (1.1 ml) at 100° C. Upon cooling to room temperature a dense precipitate is obtained, which is diluted with 11 ml of diethyl ether. After stirring for 4 hours, the white solid is recovered by filtration and dried overnight under vacuum at 80° C., to give 0.49 g of the pure product, m.p. 162–164° C.

TLC (silica gel, eluant methylene chloride/methanol 89:11; UV detection at 254 nm): single spot at $R_f$=0.45.

Elem. Anal. (% calcd/found): C 55.62/55.36; H 4.67/4.68; N 9.98/9.87; Cl 12.63/12.83.

The following compounds were prepared using the method of example 3.

The products were characterized by mass spectrometry (atmospheric pressure chemical ionization (APCI)) and tlc using silica gel and LAE (hexane/acetone/acetic acid 60:40:1) or MAE (dichloromethane/acetone/acetic acid 80:20:3) as eluant.

a) 1-[2-(4-Chloro-phenyl)-1,1-dimethyl-ethyl]-3-(5-oxo-2,5-dihydro-furan-3-yl)-urea
    MS (APCI): [M+1]=309, [M−CO$_2$+H]=265
    tlc: MAE, $R_f$=0.53
b) 1-(2-Ethyl-phenyl)-3-(5-oxo-2,5-dihydro-furan-3-yl)-urea
    MS (APCI): [M+1]=247, [M−CO$_2$+H]=203
    tlc: MAE, $R_f$=0.48
c) 1-(2,3-Dimethyl-phenyl)-3-(5-oxo-2,5-dihydro-furan-3-yl)-urea
    MS (APCI): [M+1]=247, [M−CO$_2$+H]=203
    tlc: MAE, $R_f$=0.4
d) 1-(2,4-Dimethyl-phenyl)-3-(5-oxo-2,5-dihydro-furan-3-yl)-urea
    MS (APCI): [M+1]=247, [M−CO$_2$+H]=203
    tlc: MAE, $R_f$=0.36
e) 1-(4-Ethoxy-phenyl)-3-(5-oxo-2,5-dihydro-furan-3-yl)-urea
    MS (APCI): [M+1]=263, [M−CO$_2$+H]=219
    tlc: MAE, $R_f$=0.18
f) 1-(4-Fluoro-benzyl)-3-(5-oxo-2,5-dihydro-furan-3-yl)-urea
    MS (APCI): [M+1]=251, [M−CO$_2$+H]=207
    tlc: MAE, $R_f$=0.13
g) 1-(5-Oxo-2,5-dihydro-furan-3-yl)-3-p-tolyl-urea
    MS (APCI): [M+1]=233 [M−CO$_2$+H]=189
    tlc: MAE, $R_f$=0.23
h) 1-(5-Oxo-2,5-dihydro-furan-3-yl)-3-m-tolyl-urea
    MS (APCI): [M+1]=233, [M−CO$_2$+H]=189
    tlc: MAE, $R_f$=0.23
i) 1-Cyclohexyl-3-(5-oxo-2,5-dihydro-furan-3-yl)-urea
    MS (APCI): [M+1]=225, [M−CO$_2$+H]=181
    tlc: MAE, $R_f$=0.45
j) 1-(4-Bromo-phenyl)-3-(5-oxo-2,5-dihydro-furan-3-yl)-urea
    MS (APCI): [M+1]=297, [M−CO$_2$+H]=253
    tlc: MAE, $R_f$=0.36
k) 1-(2-Fluoro-phenyl)-3-(5-oxo-2,5-dihydro-furan-3-yl)-urea
    MS (APCI): [M+1]=237, [M−CO$_2$+H]=193
    tlc: MAE, $R_f$=0.54
l) 1-(5-Chloro-2-methyl-phenyl)-3-(5-oxo-2,5-dihydro-furan-3-yl)-urea
    MS (APCI): [M+1]=267, [M−CO$_2$+H]=223
    tlc: MAE, $R_f$=0.39
m) 1-(3-Chloro-benzyl)-3-(5-oxo-2,5-dihydro-furan-3-yl)-urea
    MS (APCI): [M+1]=267, [M−CO$_2$+H]=223
    tlc: MAE, $R_f$=0.54
n) 1-(4-Chloro-phenyl)-3-(5-oxo-2,5-dihydro-furan-3-yl)-urea
    MS (APCI): [M+1]=253, [M−CO$_2$+H]=209
    tlc: MAE, $R_f$=0.4

EXAMPLE 4

4-[3-(5-Oxo-2,5-dihydro-furan-3-yl)-ureido]-benzoic acid

A mixture of 180 mg 4-carbonxy-phenyl-urea, 250 mg tetronic acid and 0.2 ml nitromethane was heated to 120° C. After 1 h at 120° C. the molten mixture is cooled to room temperature. Ethylacetate and water were added to the mixture. The organic phase was separated, washed with aqueous bicarbonate solution and water, dried and evaporated. The residue was triturated with ethylacetate and ether to yield 131 mg (51%) of the title product.

Tlc: (silica gel, isopropanol/butylacetate/water 10:6:2) $R_f$=0.62

MS (APCI): [M+1]=263, [M−CO$_2$+1]=219

EXAMPLE 5

The following compounds were prepared using the method of example 4. The products were characterized by mass spectrometry (atmospheric pressure chemical ionization) and tlc using silica gel and LAE (hexane/acetone/acetic acid 60:40:1), MAE (dichloromethane/acetone/acetic acid 80:20:3) or IBW (isopropanol/butyl acetate/water 10:6:2) as eluant.

a) 1-(3-Chloro-2-methyl-phenyl)-3-(5-oxo-2,5-dihydro-furan-3-yl)-urea
    MS (APCI): [M+1]=267, [M−CO$_2$+H]=223
    tlc: MAE, $R_f$=0.38
b) 1-(5-Oxo-2,5-dihydro-furan-3-yl)-3-(3-trifluoromethyl-phenyl)-urea
    MS (APCI): [M+1]=287, [M- CO$_2$+H]=243
    tlc: MAE, $R_f$=0.34
c) 1-(3-Bromo-phenyl)-3-(5-oxo-2,5-dihydro-furan-3-yl)-urea
    MS (APCI): [M+1]=297, [M- CO$_2$+H]=253
    tlc: LAE, $R_f$=0.27
d) 1-(2-Bromo-phenyl)-3-(5-oxo-2,5-dihydro-furan-3-yl)-urea
    MS (APCI): [M+1]=297, [M- CO$_2$+H]=253
    tlc: LAE, $R_f$=0.6
e) 1-Benzyl-3-(5-oxo-2,5-dihydro-furan-3-yl)-urea
    MS (APCI): [M+1]=233, [M- CO$_2$+H]=189
    tlc: MAE, $R_f$=0.16
f) 1-(5-Oxo-2,5-dihydro-furan-3-yl)-3-o-tolyl-urea
    MS (APCI): [M+1]=233, [M- CO$_2$+H]=189
    tlc: MAE, $R_f$=0.28
g) 1-(3-Methoxy-phenyl)-3-(5-oxo-2,5-dihydro-furan-3-yl)-urea
    MS (APCI): [M+1]=249, [M- CO$_2$+H]=205
    tlc: MAE, $R_f$=0.16
h) 1-(3-Chloro-4-methyl-phenyl)-3-(5-oxo-2,5-dihydro-furan-3-yl)-urea MS (APCI): [M+1]=267, [M- $CO_2$+H]=223
tlc: MAE, $R_f$=0.3 i) 1-(2,3-Dichloro-phenyl)-3-(5-oxo-2,5-dihydro-furan-3-yl)-urea
MS (APCI): [M+1]=288, [M- $CO_2$+H]=244
tlc: MAE, $R_f$=0.4 j) 1-(3-Chloro-phenyl)-3-(5-oxo-2,5-dihydro-furan-3-yl)-urea
MS (APCI): [M+1]=253, [M- $CO_2$+H]=209
tlc: MAE, $R_f$=0.24 k) 1-Naphthalen-1-yl-3-(5-oxo-2,5-dihydro-furan-3-yl)-urea
MS (APCI): [M+1]=269, [M- $CO_2$+H]=225
tlc: MAE, $R_f$=0.34 l) 1-[4-(3-Chloro-5-trifluoromethyl-pyridin-2-yloxy)-phenyl]-3-(5-oxo-2,5-dihydro-furan-3-yl)-urea
MS (APCI): [M+1]=414, [M- $CO_2$+H]370
tlc: LAE, $R_f$=0.28 m) 1-(3,4-Dichloro-phenyl)-3-(5-oxo-2,5-dihydro-furan-3-yl)-urea
MS (APCI): [M+1]=287, [M- $CO_2$+H]=243
tlc: MAE, $R_f$=0.32 n) 1-(4-Acetyl-phenyl)-3-(5-oxo-2,5-dihydro-furan-3-yl)-urea
MS (APCI): [M+1]=261, [M- $CO_2$+H]j =217
tlc: IBW, $R_f$=0.61 o) 1-(3-Acetyl-phenyl)-3-(5-oxo-2,5-dihydro-furan-3-yl)-urea
MS (APCI): [M+1]=261, [M- $CO_2$+H]=217
tlc: MAE, $R_f$=0.68

EXAMPLE 6

According to the methods described in the previous examples, the following furanone derivatives are prepared:

a) 4-[N-(4-fluorophenyl)aminocarbonylamino]-2(5H)-furanone;
b) 4-[N-(4-chloro-3-ethylphenyl)aminocarbonylamino]-2(5H)-furanone;
c) 4-[N-(4-tert-butyl-3 fluorophenyl)aminocarbonylamino]-2(5H) - furanone;
d) 4-[N-(4-hydroxyphenyl)aminocarbonylamino]-2(5H)-furanone;
e) 4-[N-(4-aminophenyl)aminocarbonylamino]-2(5H)-furanone;
f) 4-[N-(4-diethylaminophenyl)aminocarbonylamino]-2(5H.)-furanone;
g) 4-[N-(3-carboxyphenyl)aminocarbonylamino]-2(5H)-furanone;
h) 4-[N-(3-methoxycarbonylphenyl)aminocarbonylamino]2(5H)-furanone;
i) 4-[N-(3-acetyl-4-fluorophenyl)amnocarbonylamino]-2(5H)-furanone;
j) 4-[N-(4-aminosulphonylphenyl)aminocarbonylamino]-2(5H)-furanone;
k) 4-[N-(4-methansulphonamidophenyl)aminocarbonylamino]-2(5H)-furanone;
l) 4-[N-(4-tolylsulphonamidophenyl)aminocarbonylamino]-2(5H)-furanone;
m) 4-[N-(2,4-difluorophenyl)aminocarbonylamino]-2(5H)-furanone;
n) 4-[N-(4-ethyl-2-chlorophenyl)aminocarbonylamino]-2(5H)-furanone;
o) 4-[N-(isopropyl)aminocarbonylamino]-2(5H)-furanone;
p) 4-[N-(tert-butyl)aminocarbonylamino]-2(5H)-furanone;
q) 4-[N-(octyl)aminocarbonylamino]-2(5H)-furanone;
r) 4-[N-(cyclopropyl)aminocarbonylamino]-2(5H)-furanone;
s) 4-[N-(cyclohexyl)aminocarbonylamino]-2(5H)-furanone;
t) 4-[N-(2-pyridinyl)aminocarbonylamino]-2(5H)-furanone;
u) 4-[N-(1-isoquinolinyl)aminocarbonylamino]-2(5H)-furanone;
v) 4-[N-(3-quinolinyl)aminocarbonylamino]-2(5H)-furanone;
w) 4-[N-(3-indolyl)aminocarbonylamino]-2(5H)-furanone;
x) 4-[N-(2-thienyl)aminocarbonylamino]-2(5H)-furanone;
y) 4-[N-(2-pyrrolidinyl)aminocarbonylamino]-2(5H)-furanone;
z) 4-[N-(2-furanyl)aminocarbonylamino]-2(5H)-furanone;
aa) 4-[N-(2-imidazolyl)aminocarbonylamino]-2(5H.)-furanone;
bb) 4-[N-(2-pyrrolyl)aminocarbonylamino]-2(5H)-furanone;
cc) 4-[N-(4-ethyl-3-chlorophenyl)aminocarbonylamino]-3-methyl-2(5H)-furanone;
dd) 4-[N-(4-ethyl-3-chlorophenyl)aminocarbonylamino]-3,5-dimethyl-2(5H)-furanone;
ee) 4-[N-(4-ethyl-3-chlorophenyl)aminocarbonylamino]-5-methyl-2(5H)-furanone;
ff) 4-[N- (4-chlorophenyl)aminocarbonylamino]-3-ethyl-2(5H)-furanone;
gg) 4-[N-(4-chlorophenyl)aminocarbonylamino]-5-propyl-2(5H)-furanone.
hh) 4-[N-(4-ethyl-3-chlorophenyl)aminothiocarbonylamino]-2(5H)-furanone;
ii) 4-[N-(4-chlorophenyl)aminothiocarbonylamino]-2-(5H)-furanone;
jj) 4-[N-(4-fluorophenyl)aminothiocarbonylamino]-2(5H)-furanone;
kk) 4-[N-(4-chloro-3-ethylphenyl)aminothiocarbonylamino]-2(5H)-furanone;
ll) 4-[N-(4-tert-butyl-3-fluorophenyl)aminothiocarbonylamino]-2(5H)-furanone;
mm) 4-[N-(4-hydroxyphenyl)aminothiocarbonylamino]-2(5H)-furanone;
nn) 4-[N-(tert-butyl)aminothiocarbonylamino]-2(5H)-furanone;
oo) 4-[N-(octyl)aminothiocarbonylamino]-2(5H)-furanone;
pp) 4-[N-(cyclopropyl)aminothiocarbonylamino]-2(5H)-furanone;
qq) 4-[N-(cyclohexyl)aminothiocarbonylamino]-2(5H)-furanone;
rr) 4-[N-(2-pyridinyl)aminothiocarbonylamino]-2(5H)-furanone;
ss) 4-[N-(1-isoquinolinyl)aminothiocarbonylamino]-2(5H)-furanone;
tt) 4-[N-(3-quinolinyl)aminothiocarbonylamino]-2(5H)-furanone;

uu) 4-[N-(3-indolyl)aminothiocarbonylamino]-2(5H)-furanone;

vv) 4-[N-(2-,thienyl)aminothiocarbonylamino]-2(5H)-furanone.

EXAMPLE 7

4-(4'-cyanomethylphenylureido)-2(5H)-furanone

In a Bask equipped with a Dean-Stark apparatus, a mixture of N-(4-cyanomethyl)phenylurea (240 mg) and tetronic acid (140 mg) in toluene (3 ml) is heated at reflux for one hour. After cooling to room temperature the solid is filtered off and suspended in boiling absolute ethanol (5 ml) for 30'.

After 2 hours at 20° C. the solid is recovered by filtration and recrystallized from methanol (5 ml), to give 190 mg of product.

| | |
|---|---|
| m.p. | : 239° C. |
| E.A. found % (calculated %) | : C 60.56 (60.7); H 4.28 (4.31); N 16.22 (16.33). |
| $^1$H-NMR (DMSO-$d_6$; δ) | : 3.9 (s, 2H); 5.1 (s, 2H); 5.6 (s, 1H); 7.4 (dd, 4H); 9.2 (s, 1H); 9.8 (s, 1H) |

EXAMPLE 8

4-(3',4',5'-trimethoxyphenylureido)-2(5H)-furanone

A mixture of 3,4,5-trimethoxyphenylurea (400 mg) and ethyl-4-chloroacetoacetate (350 mg) in dioxane (0.8 ml) is heated at reflux for 4 hours. After one hour at 25° C. the precipitate is recovered by filtration and recrystallized from methanol (3 ml), to give 210 mg of product.

| | |
|---|---|
| m.p. | : 210–212° C. (with decomposition). |
| E.A. found % (calculated % for $C_{14}H_{16}O_6N_2$ × 0.5 $H_2O$) | : C 52.91 (52.99); H 5.43 (5.40); N 8.83 (8.74). |
| $^1$H-NMR (DMSO-$d_6$; δ) | : 3.6 (s, 3H); 3.75 (s, 6H); 5.1 (s, 2H), 5.55 (s, 1H), 6.7 (s, 2H); 9.1 (s, 1H); 9.8 (s, 1H). |

EXAMPLE 9

4-[N-(4-ethyl-3-chlorophenyl)aminocarbonylamino]-2(5H)-thiophenone

In a flask equipped with a Dean-Stark apparatus 3-chloro-4-ethylphenylurea (338 mg) was suspended in toluene (4 mL), then 4-hydroxy-2-(5H)thiophenone was added together with a catalytic amount of p-toluenesulfonic acid (3 mg). The resultant mixture was refluxed for about three hours then it was cooled at 60° C. and the precipitated solid filtered off.

The so obtained crude material was purified by column chromatography (SiO$_2$, eluent CH$_2$Cl$_2$/AcOEt 1:1) to yield pure 4-(3'-chloro-4'-ethylphenylureido)-(5H)-2- thiophenone (98 mg).

| | |
|---|---|
| m.p. | : 244–245° C. |
| E.A. found % (calculated %) | : C 52.3 (52.61); H 4.39 (4.42); N 9.29 (9.44); Cl 11.74 (11.95); S 10.87 (10.80) |
| $^1$H-NMR (DMSO-$d_6$; δ) | : 1.1 (t, 3H, CH$_3$—); 2.65 (q, 2H, CH$_2$-Ph); 4.4 (s, 2H, CH$_2$—S); 6.3 (s, 1H, =CH—CO); 7.25 (bs, 2H, Ph); 7.65 (bs, 1H, Ph); 9.15 (s, 1H, NH-Ph); 9.75 (s, 1H, NH—C=) |

Analogously the following compounds are prepared:

| a) 4-[(phenyl)aminocarbonylamino]-2(5H)-thiophenone | |
|---|---|
| m.p. | : 216–219° C. |
| E.A. found % (calculated %) | : C 57.3 (56.39); H 4.29 (4.30); N 10.93 (11.96); S 14.47 (13.69) |
| $^1$H-NMR (DMSO-$d_6$; δ) | : 4.3 (s, 2H, CH$_2$—S); 6.3 (s, 1H, =CH—CO); 7.05 (t, 1H, Ph); 7.3 (t, 2H, Ph); 7.4 (d, 2H, Ph); 9.05 (s, 1H, NH-Ph); 9.7 (s, 1H, NH-C=) |

| b) 4-[(4-chlorophenyl)aminocarbonylamino]-2(5H)-thiophenone | |
|---|---|
| m.p. | : 258–260° C. |
| E.A. found % (calculated %) | : C 49.09 (49.17); H 3.25 (3.38); N 10.4 (10.42); Cl 13.2 (13.19); S 11.87 (11.93) |
| $^1$H-NMR (DMSO-$d_6$; ?) | : 4.3 (s, 2H, CH$_2$—S); 6.3 (s, 1H, =CH—CO); 7.4 (dd, 4H, Ph); 9.2 (s, 1H, NH-Ph); 9.7 (s, 1H, NH—C=) |

EXAMPLE 10

According to the methods described in the previous examples, the following thiophenone derivatives are prepared:

a) 4-[N-(4-fluorophenyl)aminocarbonylamino]-2(5H)-thiophenone;

b) 4-[N-(4-bromophenyl)aminocarbonylamino]-2(5H)-thiophenone;

c) 4-[N-(4-chloro-3-ethylphenyl)aminocarbonylamino]-2(5H)-thiophenone;

d) 4-[N-(4-methylphenyl)aminocarbonylamino]-2(5H)-thiophenone;

e) 4-[N-(3-chlorophenyl)aminocarbonylamino]-2(5H)-thiophenone;

f) 4-[N-(3-bromophenyl)aminocarbonylamino]-2(5H)-thiophenone;

g) 4-[N-(3-trifluoromethylphenyl)aminocarbonylamino]-2(5H)-thiophenone;

h) 4-[N-(3-methoxyphenyl)aminocarbonylamino]-2(5H)-thiophenone;

i) 4-[N-(3-carboxyphenyl)aminocarbonylamino]-2(5H)-thiophenone;

j) 4-[N-(3-chloro-4-methylphenyl)aminocarbonylamino]-2(5H)-thiophenone;

k) 4-[N-(3,4-dichlorophenyl)aminocarbonylamino]-2(5H)-thiophenone;

l) 4-[N-(3-chloro-4-trifluoromethylphenyl)aminocarbonylamino]-2(5H)-thiophenone;

m) 4-[N-(2-bromophenyl)aminocarbonylamino]-2(5H)-thiophenone;

n) 4-[N-(2-methylphenyl)aminocarbonylamino]-2(5)-thiophenone o) 4-[N-(4-aminosulphonylphenyl)aminocarbonylamino]-2(5H)-thiophenone;

p) 4-[N-(4-methansulphonamidophenyl)aminocarbonylamino]-2(5H)-thiophenone;

q) 4-[N-(4-tolylsulphonamidophenyl)aminocarbonylamino]-2(5H)-thiophenone;

r) 4-[N-(2-fluorophenyl)aminocarbonylamino]-2(5H)-thiophenone;

s) 4-[N-(2,4-difluorophenyl)aminocarbonylamino]-2(5H)-thiophenone;

t) 4-[N-(4-ethyl-2-chlorophenyl)aminocarbonylamino]-2(5H)-thiophenone;

u) 4-[N-(isopropyl)aminocarbonylamino]-2(5H)-thiophenone;

v) 4-[N-(cyclopropyl)aminocarbonylamino]-2(5H)-thiophenone;

w) 4-[N-(2-pyridinyl)aminocarbonylamino]-2(5H)-thiophenone;

x) 4-[N-(I-isoquinolinyl)aminocarbonylamino]-2(5H)-thiophenone;

y) 4-[N-(3-quinolinyl)aminocarbonylamino]-2(5H)-thiophenone;

z) 4-[N-(3-indolyl)aminocarbonylamino]-2(5H)-thiophenone;

aa) 4-[N-(2-thienyl)aminocarbonylamino]-2(5H)-thiophenone;

bb) 4-[N-(2-pyrrolidinyl)aminocarbonylamino]-2(5H)-thiophenone;

cc) 4-[N-(2-furanyl)aminocarbonylamino]-2(5H)-thiophenone;

dd) 4-[N-(4-ethyl-3-chlorophenyl)aminocarbonylamino]-3-methyl-2(5H)-thiophenone;

ee) 4-[N-(4-ethyl-3-chlorophenyl)aminocarbonylamino]-3,5-dimethyl-2(5H)-thiophenone;

ff) 4-[N-(4-ethyl-3-chlorophenyl)aminocarbonylamino]-5-methyl-2(5H)-thiophenone;

gg) 4-[N-(4-chlorophenyl)aminocarbonylamino]-3-ethyl-2(5H)-thiophenone;

hh) 4- [N, -.(4-chlorophenyl)aminocarbonylamino]-5-propyl -2(5 H)-thiophenone.

ii) 4-[N-(4-ethyl-3-chlorophenyl)aminothiocarbonylamino]-2(5H)-thiophenone;

jj) 4-[N-(4-chlorophenyl)aminothiocarbonylamino]-2(5H)-thiophenone;

kk) 4-[N-(4-fluorophenyl)aminothiocarbonylamino]-2(5H)-thiophenone;

ll) 4-[N-(4-chloro-3-ethylphenyl)aminothiocarbonylamino]-2(5H)-thiophenone;

What is claimed is:

1. A method of treating a tumor in a patient in need thereof, comprising administering to said patient an antitumor effective amount of a compound of the general formula (I):

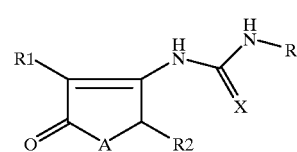

(I)

wherein:
A is oxygen or sulfur;
X is oxygen or sulfur;
R1 and R2 are independently hydrogen or an alkyl group with from 1 to 6 carbon atoms;
R is selected from: ($C_1$–C10)alkyl, (C3–$C_7$)cycloalkyl, ($C_1$–$C_4$)alkylthio, ($C_1$–$C_4$)alkylsulphinyl, ($C_1$–$C_4$)alkylsulphonyl, ($C_1$–$C_4$)hydroxyalkyl, naphthyl, phenyl, phenyl substituted by from 1 to 3 groups selected from: ($C_1$–$C_4$)alkyl; chlorine, bromine, iodine or fluorine; ($C_1$–$C_4$)perfluoroalkyl; hydroxy; ($C_1$–$C_4$)alkoxy; amino; mono- or di-($C_1$–$C_4$)alkylamino; aminosulphonyl;($C_1$–$C_4$)alkylsulphonamido; phenyl- or tolyl-sulphonamido; carboxy; ($C_1$–$C_4$)alkoxycarbonyl; amidocarbonyl or ($C_1$–$C_4$)alkylamidocarbonyl; carboxaldehyde; ($C_1$–$C_4$)alkylcarbonyl; nitro; phenylthio; cyanomethyl, and optionally substituted phenyloxy or optionally substituted phenyl—($C_1$–$C_4$)—alkyl or R is a 5- or 6-membered aromatic or non-aromatic heterocycle containing from 1 to 3 heteroatoms selected from oxygen, sulfur and nitrogen, which can be optionally benzocondensed, the pure stereoisomers or mixtures thereof as well as salts thereof with pharmaceutically acceptable acids or bases, with the proviso, that when, A is oxygen and X is oxygen, R is not $C_1$–$C_{10}$)alkyl.

2. The method of treating a tumor according to claim 1, further comprising administering a medicament wherein the medicament comprises the compound of general formula (I) as an active agent.

3. Pharmaceutical compositions containing a pharmaceutically effective amount of one or more compounds of formula (I) as depicted claim 1, in admixture with pharmaceutically acceptable eccipients.

4. A process for the preparation of the compounds according to claim 1, which comprises reacting a compound of formula (VII):

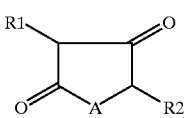

(VII)

wherein A is oxygen or sulfur and $R_1$ and $R_2$ have the meanings mentioned above, with an urea or thiourea of formula (III):

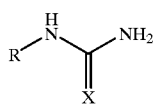

(III)

in which R and X have the meanings mentioned above, in a solvent at reflux.

5. A method of preparing a medicament possessing antitumor activity comprising the compounds of formula (I) wherein said method comprises (a) providing at least one compound of formula (I), and (b) admixing therapeutically effective amounts of the at least one compound with pharmaceutically acceptable ingredients to prepare a medicament capable of oral, intravenous, intramuscular or subcutaneous administration,

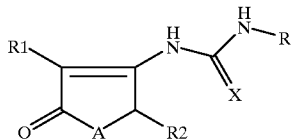 (I)

wherein:

A is oxygen or sulfur;

X is oxygen or sulfur;

R1 and R2 are independently hydrogen or an alkyl group with from 1 to 6 carbon atoms;

R is selected from: $(C_1-C_{10})$alkyl, $(C_3-C_7)$cycloalkyl, $(C_1-C_4)$alkylthio, $(C_1-C_4)$alkylsulphinyl, $(C_1-C_4)$alkylsulphonyl, $(C_1-C_4)$hydroxyalkyl, naphthyl, phenyl, phenyl substituted by from 1 to 3 groups selected from: $(C_1-C_4)$alkyl; chlorine, bromine, iodine or fluorine; $(C_1-C_4)$perfluoroalkyl; hydroxy; $(C_1-C_4)$alkoxy; amino; mono- or di-$(C_1-C_4)$alkylamino; aminosulphonyl; $(C_1-C_4)$alkylsulphonamido; phenyl- or tolylsulphonamido; carboxy; $(C_1-C_4)$alkoxycarbonyl; amidocarbonyl or $(C_1-C_4)$alkylamidocarbonyl; carboxaldehyde; $(C_1-C_4)$alkylcarbonyl; nitro; phenylthio; cyanomethyl, and optionally substituted phenyloxy or optionally substituted phenyl-$(C_1-C_4)$alkyl or R is a 5- or 6-membered aromatic or non-aromatic heterocycle containing from 1 to 3 heteroatoms selected from oxygen, sulfur and nitrogen, which can be optionally benzocondensed, the pure stereoisomers or mixtures thereof as well as salts thereof with pharmaceutically acceptable acids or bases, with the proviso, that when A is oxygen and X is oxygen, R is not $C_1-C_{10}$alkyl.

* * * * *